United States Patent
Armistead

(10) Patent No.: US 8,096,986 B2
(45) Date of Patent: Jan. 17, 2012

(54) BARB-ENDED, SELF-ACTUATING, PARTIALLY INDWELLING AND CONTINUALLY RETAINED URINARY CATHETER

(76) Inventor: John Anderson Armistead, Easley, SC (US)

( * ) Notice: Subject to any disclaimer, the term of this patent is extended or adjusted under 35 U.S.C. 154(b) by 208 days.

(21) Appl. No.: 12/583,572

(22) Filed: Aug. 24, 2009

(65) Prior Publication Data

US 2010/0312226 A1    Dec. 9, 2010

(51) Int. Cl.
*A61M 27/00* (2006.01)
(52) U.S. Cl. .................. 604/544; 604/256; 604/264
(58) Field of Classification Search ................ 604/256, 604/264, 175, 500, 508, 523, 540–544; 600/29, 600/30; 264/478; 128/349 R
See application file for complete search history.

(56) References Cited

U.S. PATENT DOCUMENTS

| | | | | |
|---|---|---|---|---|
| 1,644,919 A | * | 10/1927 | Hayes | 606/180 |
| 1,888,349 A | * | 11/1932 | Jacoby | 604/256 |
| 3,419,008 A | * | 12/1968 | Plishner | 600/31 |
| 3,428,046 A | * | 2/1969 | Vagenius et al. | 604/265 |
| 3,812,841 A | * | 5/1974 | Isaacson | 600/29 |
| 4,306,566 A | * | 12/1981 | Sinko | 600/435 |
| 4,909,785 A | * | 3/1990 | Burton et al. | 604/544 |
| 5,007,897 A | * | 4/1991 | Kalb et al. | 604/43 |
| 6,221,060 B1 | * | 4/2001 | Willard | 604/264 |
| 7,857,807 B2 | * | 12/2010 | Wang | 604/544 |
| 2002/0045855 A1 | * | 4/2002 | Frassica | 604/109 |
| 2005/0192560 A1 | * | 9/2005 | Walls et al. | 604/544 |

* cited by examiner

*Primary Examiner* — Tatyana Zalukaeva
*Assistant Examiner* — Benedict L Hanrahan

(57) ABSTRACT

While waiting for prostate-size-reducing drugs or herbs to have an effect, it's often necessary to have a catheter, like the Foley, inserted into the bladder. Urine passing through such collects in a plastic bag which must be drained, regularly, and is awkward to carry and difficult to disguise under clothing. In lieu of a Foley, full-length self-cathetering is less awkward, but the recurring process can irritate the urethra and prostate, and increase the chance of getting cystitis. The present new catheter type has a barb-like tip to retain such inside the bladder. A urine drainage inlet is located less than an inch below the barb. The easy drainage of urine is facilitated simply by pushing the catheter upward until the inlet opening is inside the bladder. Because the required insertion distance is much reduced, there's less likelihood of there being irritation of the organs, and less likelihood of getting cystitis.

1 Claim, 1 Drawing Sheet

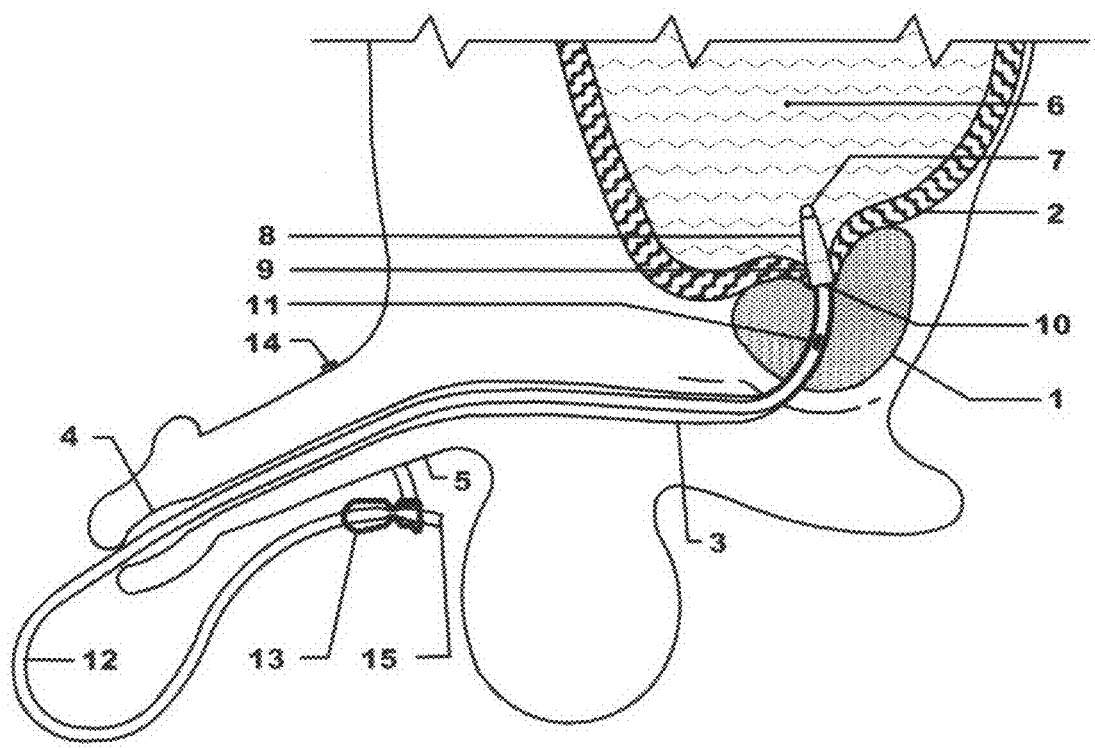

BARB-ENDED, SELF-ACTUATING, PARTIALLY INDWELLING AND CONTINUALLY RETAINED URINARY CATHETER

CROSS REFERENCE TO RELATED APPLICATIONS

Another patent by this inventor, application Ser. No. 12/455,485, has similar medical objectives, but uses different means for achieving such. The present application will cover the generalities of the medical objectives, as well as describing in detail the functionality of the invention.

BACKGROUND OF THE INVENTION

Urinary retention due to an enlarged prostate gland necessitates catheterization or surgery to allay possible kidney damage. Drugs that can shrink the prostate or relieve some of the constriction in the muscles that bound the gland can take months to have a notable effect. During such time, a catheter, such as the Foley, must be kept in place. Or the individual may choose to use a removable 'self catheter' repeatedly, day and night, whenever urine accumulation in the bladder dictates.

A Foley catheter provides continuous drainage into a collection bag. The latter is a hindrance to carry, drain, and disguise within clothing. Because of likely tugs on the catheter due to the collection bag and its tubing, there is an inflated bulb on a Foley. Such is most effective in preventing the unintentional slippage of the catheter from the body. But that bulb necessitates that the urine inlet slots be located from 1" to 1½" above the bottom of the bladder. If there is bleeding anywhere in the bladder, coagulated blood can accumulate below the bulb, and can cause blockage of the tube inlets, as when the user lies down. And because the Foley catheter is essentially unmoved once inserted, there is a chance that such can become incrusted with mineral deposits that could make a Foley difficult to remove.

Self-cathetering eliminates the hindrance of a bulky urine collection bag and its tubing, but entails repeated insertion of a semi-hard rubber tube through the urethra. There can be pain and irritation from the friction of that catheter type, even when well lubricated. And there is a high probability of introducing bacteria into the bladder, causing uncomfortable cystitis. When there is infection or irritation, the threshold of urine build-up—before getting the urge to void the bladder—is lowered. For that reason, self-cathetering can exacerbate problems which it was hoped would be lessened.

As with self-cathetering, the present invention drains urine from the bladder whenever the user feels the urge of an accumulation. But unlike with self-cathetering, such drainage can be actuated by as little as one inch of upward insertion of that left-in-place tube. The greatly shortened insertion distance is made possible because the drainage inlet of the tube is located below a retaining, barb-like metal tip. The constriction of the prostate gland itself prevents urine from flowing into the inlet slot until such slot is intentionally pushed up into the urine pool by the user. After doing so, urine can flow out the distal end of the tubing, once a stock tubing clamp has been opened.

Because of the much reduced insertion distance, the chance that bacteria can be pushed into the bladder is reduced, too—as is the pain and involvement in time and preparation for inserting a long tube each time voiding is needed. Because the tubing gets moved, regularly, the chance that mineral deposits will form is lessened—allowing this new catheter type to remain in place for longer periods than a Foley. When removal is desired, the size of the barb end of the metal tip is small enough to allow the catheter to be slowly pulled out. The eased edges of the barb will reduce the chance of injury to the urethra in doing so.

Conceptually, a sterile-water-inflated bulb can be substituted for the metal barb in the present embodiment of this invention, provided the urine inlet slot(s) is located well below the bulb, and there is sufficient catheter length beyond the tip of the penis to allow that variant of catheter to be pushed upward for actuating the catheter, while allowing room for a tubing clamp. The latter is needed to prevent leaks as could happen when the prostate and its musculature change over time due to the drugs being taken or other causal factors.

BRIEF SUMMARY OF THE INVENTION

A semi-hard rubber catheter tube has a gold-plated, machined brass, cone-shaped barb bonded onto its upper end. The cone shape facilitates having the barb be inserted upward through the urethra. But the blunt, back end of the barb resists letting the catheter fall out once such has past the sphincter muscles at the bladder outlet. An inlet slot is located less than an inch below the back of the barb. Tightness in the sphincter muscle and in the enlarged prostate prevent urine from draining into the inlet slot. Additionally, there is a stock tubing clamp on the distal end of the tubing to prevent leakage until the inlet hole has been pushed up into the bladder and the clamp is intentionally opened. The catheter is actuated by the user slowly pushing the tubing upward until the drainage slot is within the urine pool. Urine will flow out until drained and stop on its own. The weight of the brass barb, plus the 'expulsion' contractions of the urethra, will return the barb to its former position. The entire drainage process is quicker and less painful than with a self-catheter. And there is also reduced risk of introducing bacteria into the bladder. That's because the 'handled' portion of the tubing for actuating bladder drainage never gets pushed into the bladder. The portion of tubing that is handled can be lubricated and cleaned with tap water after washing the hands.

BRIEF DESCRIPTION OF THE VIEW OF THE DRAWING

The schematic drawing is a vertical section cut through a typical man's penis, prostate, and bladder. The catheter is shown as if in elevation (rather than in section) because the concept of a rubber tube that has a bonded metal barb on the end doesn't require a sectional drawing to be understood. The invention can be explained in a single drawing, because the process of having the user push the catheter, with its barb and the slot below, up into the urine pool to facilitate drainage, is easy to visualize from words alone.

DETAILED DESCRIPTION OF THE INVENTION

An enlarged prostate, 1, can restrict urine flow and cause urine, 6, to overly distend the bladder, 2. The present invention provides a catheter, 12, threaded through the tip of the penis, 4, which is a firm enough tube to maintain a reliable passage through the enlarged prostate, 1. Unlike a Foley catheter that has a sterile-water-inflated bulb located within the bladder, 2, the present embodiment of the invention has a gold-plated, unitary, machined brass barb, 8, 9, and 10. Because the latter is largest on the back end, 10, the resistance to having the catheter, 12, slip out is several times greater than the effort needed to insert the cone-shaped tip, 8.

The gold-plated, unitary, machined brass barb, 8, 9, and 10, is bonded to the bullet-like end, 7, of the plastic or rubber catheter, 12. The bullet-like end, 7, serves to help to ease the barb through the penis tip, 4; the urethra, 3; and the enlarged prostate, 1. Once inside the bladder, 2, the gold-plated, unitary, machined brass barb, 8, 9, and 10, can seat itself against, or slightly inside of the muscular outlet of the bladder. A cylindrical machined portion, 9, adjacent to the back end, 10, and integral with the cone portion, 8, serves to resist the compression from the bladder sphincter. If the latter were allowed to press against the cone portion, 8, there would be a slight downward sliding component of the compressive force which could cause the catheter, 12, to fall out, or to at least move downward more than would be comfortable or desirable.

A longitudinal urine drainage inlet or opposing urine drainage inlets, 11, is or are located less than an inch below the gold-plated, unitary, machined brass barb, 8, 9, and 10. In a tightly-enlarged prostate, 1, the compression around the longitudinal urine drainage inlet or the opposing urine drainage inlets, 11, is sufficient to prevent urine from leaking through the catheter, 12. Due to the effects of prostate-size-reducing drugs or herbs, or the muscle relaxing effects of drugs or for other reasons, a standard, unitary Nylon tubing clamp, 13 is positioned near the end of the catheter, 15. Such standard, unitary Nylon tubing clamp, 13, if allowed to extend down the user's pants leg, would tend to tug on the catheter, 12, and cause the gold-plated, unitary machined brass barb, 8, 9, and 10, to begin moving downward through the enlarged prostate, 1. To reduce the chances of having the catheter, 12, and its standard, unitary Nylon tubing clamp, 13 be tugged downward by entanglement in the user's pants, or for other reasons, the catheter, 12, is looped up toward the base of the penis, 5. An aptly sized rubber band, 14, fitted around the penis will greatly reduce the chance that the catheter, 12, and its standard, unitary Nylon tubing clamp, 13, will get tugged downward.

When the user experiences the urge to void—brought on by the buildup of urine, 6, in the bladder, 2—he can release the rubber band, 14, and open the standard, unitary Nylon tubing clamp, 13. With the catheter portion that extends from the penis tip, 4, to the end of the catheter, 15, dangling into a lavatory, and following the washing of the user's hands, plain tap water can be splashed onto the catheter, 12. With the catheter, 12, now cleaned and lubricated with water, the user very slowly and gently pushes the exposed part of catheter, 12, upward toward the penis tip, 4. While doing the latter, the gold-plated, unitary machined brass barb, 8, 9, and 10, will be moving upward into the urine pool, 6. Once the longitudinal urine drainage inlet or the opposing urine drainage inlets, 11, have reached the urine pool, 6, urine will be free to flow through the catheter, 12, and out of the end of the catheter, 15, into the lavatory. Once the bladder, 2, is drained, the rubber band, 14, is again positioned over the penis, to hold the catheter, 12, and its now closed standard, unitary Nylon tubing clamp, 13, in a position that is least likely to get tugged downward.

Because the portion of the catheter, 12, that must be handled in order to actuate the drainage of urine, 6, through a longitudinal drainage inlet, or opposing drainage inlets, 11, is small, the likelihood that harmful bacteria can be introduced into the enlarged prostate, 1, or into the bladder, 2, is greatly reduced. Therefore, the likelihood of the user developing cystitis will be reduced. Compared to 'self-cathetering' a full length of tubing into the bladder perhaps a dozen or more times day or night, the greatly improved ease of using the present new catheter type should be most obvious, and cause such to be preferred over either self-cathetering or using a Foley catheter with its pesky bag and the related problems already mentioned.

The invention claimed is:

1. An urinary catheter comprising:
   a rubber catheter tube with a distal end and proximal end, where the distal end is configured to be inserted into the bladder;
   a tubing clamp located on the proximal end of the catheter tube that is to remain external of the body during deployment;
   an unitary brass barb located on the distal end configured to retain the urinary catheter within the bladder;
   an urinary drainage inlet located less than one inch below the entire body of the brass barb;
   whereby the urinary catheter functions as an up-and-down movable valve that is configured to be located within a man's enlarged prostate-urethral organs, to allow the man to drain urine from the bladder by pushing the urinary catheter upward until the urinary drainage inlet is located within the bladder and to close the movable valve by pulling down on the urinary catheter; and
   once the bladder has been drained, the urinary catheter is stored by looping it up toward a base of a penis and an aptly sized rubber band is fitted around the penis to hold the urinary catheter in a position to prevent accidental dislodgement.

* * * * *